United States Patent [19]

Yoshikumi et al.

[11] 4,288,555

[45] Sep. 8, 1981

[54] METHOD FOR THE CULTIVATION OF BASIDIOMYCETES

[75] Inventors: Chikao Yoshikumi, Kunitachi; Toshihiko Wada, Mibu; Himromitsu Makita, Tokyo; Kinzaburo Suzuki, Mibu, all of Japan

[73] Assignee: Kureha Kagaku Kogyo Kabushiki Kaisha, Tokyo, Japan

[21] Appl. No.: 104,400

[22] Filed: Dec. 17, 1979

Related U.S. Application Data

[63] Continuation-in-part of Ser. No. 823,110, Aug. 9, 1977, abandoned.

[30] Foreign Application Priority Data

Aug. 24, 1976 [JP] Japan ................................. 51-100157

[51] Int. Cl.³ ............................................... C12N 1/14
[52] U.S. Cl. .................................... 435/254; 435/30; 435/803
[58] Field of Search ................. 435/254, 30, 171, 173, 435/803

[56] References Cited

U.S. PATENT DOCUMENTS 2,488,248  11/1949  Vander Brook et al. .......... 435/254
4,051,314  9/1977  Ohtsuka et al. ................. 435/803 X

OTHER PUBLICATIONS

Industrial Microbiology, pp. 515–583, (1959).

*Primary Examiner*—R. B. Penland
*Attorney, Agent, or Firm*—Wegner & Bretschneider

[57] ABSTRACT

In submerged culture of a Basidiomycete belonging to the genus Coriolus, the seed culture to be inoculated into the medium is homogenized to form a homogenous slurry and the slurry-formed seed culture is inoculated into the medium. This improves the cultivation rate of the Basidiomycetes.

1 Claim, No Drawings

METHOD FOR THE CULTIVATION OF BASIDIOMYCETES

CROSS-REFERENCE TO RELATED APPLICATION

The present application is a continuation-in-part of application Ser. No. 823,110, filed Aug. 9, 1977, now abandoned.

BRIEF SUMMARY OF THE INVENTION

In an aspect of this invention, there is provided a method for submerged culture of the Basidiomycetes belonging to the genus Coriolus, which method is capable of increasing the cultivation rate and reducing the required cultivation period as compared with the conventional methods.

DETAILED DESCRIPTION OF THE INVENTION

This invention relates to a method for submerged culture of the Basidiomycetes which method is capable of reducing the required period of cultivation. The term "submerged culture" is used herein to mean shaking culture or aerated agitating culture. Shaking culture is usually employed for performing cultivation of seed culture in its initial stage or for small-scale production of the cultivation, while aerated agitating culture is used for relatively large-scale production by using a tank-type fermenter.

In the course of our study on this subject, we found that, in submerged culture of the Basidiomycetes, the period of cultivation of the basidiomycetes can be markedly reduced by homogenizing the seed culture into a uniform homogenous slurry to such an extent that lumps of mycelia are not recognizable externally and then inoculating the resultant slurry into a medium.

The Basidiomycetes used in this invention are those belonging to the genus Coriolus of the Polyporaceae family, and the mycological properties of these Basidiomycetes are described in "COLORED ILLUSTRATIONS OF FUNGI OF JAPAN" by Rokuya Imazeki and Tsuguo Hongo, Vols, I, 1975, and II, 1974, and "FUNGI IN JAPAN" by Seiya Itoh. Typical examples of these Basidiomycetes are *Coriolus versicolor* (Fr.) Quel., *Coriolus consors* (Berk.) Imaz., *Coriolus hirsutus* (FR.) Quel., *Coriolus pargamenus* (Fr.) Pat., *Coriolus pubesens* (Fr.) Quél. and *Coriolus conchifer* (Schw.) Pat., In the present invention, the seed culture of these Basidiomycetes for inoculation is used not in the form as just prepared but in the form of a homogenous slurry obtained by homogenizing the previously prepared seed culture. The seed culture obtained by cultivating one of the Basidiomycetes is composed of thread-form mycelia, and most of the mycelia are granular or in the form of lumps or clumps about the size of adzuki beans (such lumps being hereinafter referred to as pellets), forming an unhomogenous mixture system. To "homogenize" such a seed culture is to apply a shearing force to the pellets so as to break them up to allow the individual thread-form mycelia to be dispersed uniformly. Slight cuts in the mycelia themselves during homogenization do no harm for the purpose of this invention. There can be thus obtained a slurry where the mycelia are dispersed uniformly by the shearing force. It should therefore be understood that the homogenization treatment for the seed culture used in this invention is continued until there is obtained a slurry homogenized to such an extent that the existance of the clumps of mycelia is not recognizable externally, preferably the size of the clumps is within the range of $50-1000\mu$.

The homogenizing treatment of the seed culture is usually accomplished by using a known means such as a homogenizer, homoblender; dispersion mixer, fruit juicer or screw mixer. The time required for forming a homogenous slurry of the seed culture by such homogenization means to such an extent that no mycelium clump can be recognized externally varies depending on the kind of the Basidiomycete used and the cultivation conditions for preparing the seed culture, but is usually within the range of 30 seconds to about 10 minutes. It should be noted here that if excess shearing force is applied to the seed culture to reduce the size of the mycelia clumps to $2-3\mu \times 10-50\mu$, the mycelia could be ground resulting in an unfavorable effect on the propagation of the fungi in the ensuing cultivation.

It was found that the rotation number of the propeller of the homogenizer which causes the necessary shearing action is very important for obtaining the seed mycelia having a vigorous growing capability. After examining several condition of homogenization, it was found that the rotation number is preferably between 3,000 and 6,000 r.p.m.

The amount of seed culture inoculated into the medium for the main cultivation of the homogenous slurry seed culture is usually 0.01 to 0.2 gr, preferably 0.05 to 0.15 gr per liter of medium. When these figures are compared with those (0.3 to 1.0 g/l) required for using an ordinary non-homogenized seed culture, it is evident that the method of this invention can markedly reduce the required amount of seed culture for inoculation.

The medium used for cultivation of the Basidiomycetes by inoculating the seed culture according to the method of this invention is an aqueous medium for cultivation of the Basidiomycetes, and no particular composition is required. Also, no specific operating parameters are required for the cultivation conditions such as cultivation temperature, aeration rate and agitating speed, and ordinarily employed cultivation conditions can be applied in this invention.

Shown in the following are some embodiments of this invention, but the scope of this invention is not intended to be restricted by the examples.

EXAMPLE 1

120 liters of the medium of the following composition:

| | |
|---|---|
| Dextrose | 50 gr |
| Yeast extract | 7.5 gr |
| Water | 1 liter |
| pH: 6.5 | | was fed into a 200-liter-capacity fermenter and subjected to pressure sterilization at 120° C. according to an ordinary method. Then, the mycelia of *Coriolus versicolor* (Fr.) Quél., which had been previously cultivated in a 30-liter jar fermenter, were homogenized by a homoblender (mfd. by Sakuma Seisakujo Ltd.) for the period shown in Table 1 below until the pellets became indiscernible to the naked eye. The homogenized mycelia were inoculated into the 200-liter fermenter in the inoculation amounts shown in Table 1 and then subjected to a 150-hour cultivation at a temperature of 25° C., aeration rate of 0.5 v.v.m. and agitation speed of 250 r.p.m. The mycelia were separated from the obtained culture, washed with water, ethyl alcohol and acetone, and then dried at 80° C. The results are shown in Table 1 below.

TABLE 1

| No. | Homogen- ization treatment (time) | Seed culture inoculation amount (g/l medium) | Observation | Yield of my- celia (g/l medium) |
| --- | --- | --- | --- | --- |
| 1 | 0 | 0.011 | mycelia lumps were present | 5.5 |
| 2 | 2 min. | 0.011 | mycelia lumps existed slightly | 10.9 |
| 3 | 7 min. | 0.031 | mycelia lumps disappeared substantially | 12.9 |
| 4 | 0 | 0.100 | mycelia lumps were present | 11.6 |

It is seen from the above table that when cultivation is performed by inoculating a uniform slurry of homogenized seed culture, there can be obtained the same yield of mycelia at an inoculation amount in approximately 1/10 that required in using a non-homogenized seed culture.

EXAMPLE 2

In this example, cultivation was performed by using, in one run, a homogenized seed culture prepared according to this invention and by using, in another run a non-homogenized seed culture, and the times required for the respectively produced mycelia to reach a yield of about 11 gr per liter of medium were compared.

A seed culture of the same species as used in Example 1 was homogenized according to the same procedure as described in Example 1 and this homogenized seed culture was inoculated into a medium of the same composition as used in Example 1 and then subjected to cultivation, while in the other, the seed culture was the same species as mentioned above, but was not homogenized, was similarly inoculated and cultivated. It was found that in the case of using a uniform slurry of homogenized seed culture, the cultivation time required for attaining the 11 g/l level of mycelia yield is greatly shortened at a low inoculation amount as compared with the case of using non-homogenized seed culture.

EXAMPLE 3

One hundred and twenty liters of a culture medium of the following composition at a pH of 6.5:

| Dextrose | 50 g |
| --- | --- |
| Yeast extract | 7.5 g |
| Water | 1 liter | were placed in a fermenter of a capacity of 200 l and after sterilization at 120° C., respectively treated mycelia previously cultivated in a 30-liter jar fermenter were respectively inoculated into the culture medium in the sterilized fermenter of 200 l in capacity and then subjected to cultivation for 150 hours at a temperature of 25°±2° C., an aeration rate of 0.5 volume/volume of the fermenter min and an agitation of 250 r.p.m. After 150 hours' cultivation, the proliferated mycelia were separated from the culture medium, washed with water, ethanol and acetone in the order and then dried at 80° C. The condition of treatment of seed mycelia, the amount of seed mycelia per cultivation and the yield of proliferated mycelia are shown in Table 3.

TABLE 3:

| | Inoculation and Cultivation | | | |
| --- | --- | --- | --- | --- |
| | Inoculum | | Cultivation | |
| Run | R.P.M. in Homogen- ization (r.p.m.) | Time of Homogen- ization (min.) | Amount of Inoculum (g/l of medium) | Yield of mycelia (g/l of medium) |
| 1 | — | — | 0.01 | 5.4 |
| 2 | 1,000 | 0.5 | 0.01 | 5.5 |
| 3 | 1,000 | 1.0 | 0.01 | 5.6 |
| 4 | 1,000 | 3.0 | 0.01 | 5.6 |
| 5 | 2,000 | 2.0 | 0.01 | 8.3 |
| 6 | 3,000 | 1.0 | 0.01 | 9.4 |
| 7 | 3,000 | 2.0 | 0.01 | 9.8 |
| 8 | 3,000 | 3.0 | 0.01 | 9.8 |
| 9 | 3,000 | 5.0 | 0.01 | 9.8 |
| 10 | 4,000 | 2.0 | 0.01 | 10.0 |
| 11 | 4,000 | 3.0 | 0.01 | 10.0 |
| 12 | 4,000 | 5.0 | 0.01 | 10.2 |
| 13 | 5,000 | 2.0 | 0.01 | 10.6 |
| 14 | 5,000 | 3.0 | 0.01 | 10.6 |
| 15 | 5,000 | 5.0 | 0.01 | 10.4 |
| 16 | 6,000 | 2.0 | 0.01 | 10.0 |
| 17 | 7,000 | 2.0 | 0.01 | 9.0 |
| 18 | 7,000 | 1.0 | 0.01 | 9.1 |
| 19 | 9,000 | 2.0 | 0.01 | 7.0 |
| 20 | 9,000 | 1.0 | 0.01 | 6.8 |

What is claimed is:

1. In a method for growing a fungus *Coriolus versicolor* (Fr.) Quél. by inoculating a culture medium with a homogenized slurry of seed mycelia of said fungus and cultivating said mycelia under submerged conditions to produce growth of said fungus, the improvement comprising the steps of:

treating seed mycelial lumps of said fungus with rotating propellers in a homogenizing apparatus at a speed of 3,000 to 6,000 r.p.m. for 1.5 to 2.5 minutes, thereby reducing the size of said seed mycelial lumps to 50 to 1,000 microns and at the same time obtaining homogeneously dispersed seed mycelia in the form of threads while substantially preventing cuts into said seed mycelia inoculating said culture medium with the thus obtained seed mycelia at an inoculating rate of 0.01 to 0.2 g of said seed mycelia per liter of said culture medium, and carrying out said cultivation under submerged conditions.

* * * * *

UNITED STATES PATENT AND TRADEMARK OFFICE
CERTIFICATE OF CORRECTION

PATENT NO. : 4,288,555
DATED : September 8, 1981
INVENTOR(S) : C. YOSHIKUMI et al.

It is certified that error appears in the above—identified patent and that said Letters Patent is hereby corrected as shown below:

On the title page, Item [75],
the correct spelling of the third inventor's name is:

HIROMITSU MAKITA

Signed and Sealed this

Sixth Day of April 1982

|SEAL|

Attest:

GERALD J. MOSSINGHOFF

Attesting Officer     Commissioner of Patents and Trademarks